United States Patent
Sahbaz

(10) Patent No.: US 12,347,667 B2
(45) Date of Patent: Jul. 1, 2025

(54) METHOD OF AUTO TUNING ONE OR MORE SENSORS

(71) Applicant: INFICON, Inc., East Syracuse, NY (US)

(72) Inventor: Eldin Sahbaz, Jamesville, NY (US)

(73) Assignee: Inficon Inc., East Syracuse, NY (US)

( * ) Notice: Subject to any disclaimer, the term of this patent is extended or adjusted under 35 U.S.C. 154(b) by 0 days.

(21) Appl. No.: 18/686,753

(22) PCT Filed: Aug. 10, 2023

(86) PCT No.: PCT/US2023/029925
§ 371 (c)(1),
(2) Date: Feb. 26, 2024

(87) PCT Pub. No.: WO2024/035834
PCT Pub. Date: Feb. 15, 2024

(65) Prior Publication Data
US 2025/0166986 A1    May 22, 2025

Related U.S. Application Data

(60) Provisional application No. 63/397,471, filed on Aug. 12, 2022.

(51) Int. Cl.
*H01J 49/00* (2006.01)
*G01N 33/00* (2006.01)
*H01J 49/42* (2006.01)

(52) U.S. Cl.
CPC ...... *H01J 49/4215* (2013.01); *G01N 33/0006* (2013.01); *H01J 49/0036* (2013.01)

(58) Field of Classification Search
CPC .............. H01J 49/4215; H01J 49/0036; G01N 33/0006
(Continued)

(56) References Cited

U.S. PATENT DOCUMENTS

| 5,239,492 A | 8/1993 | Hartwig et al. |
| 2004/0113062 A1* | 6/2004 | Norton ............... G01N 30/8668 250/282 |

(Continued)

OTHER PUBLICATIONS

USPTO, International Search Report and Written Opinion of the ISA/US from Intedrnational Application No. PCT/US2023/029925, mailed Nov. 17, 2023.
(Continued)

*Primary Examiner* — Michael Maskell
(74) *Attorney, Agent, or Firm* — Barclay Damon LLP

(57) ABSTRACT

A method for automatically calibrating a sensor for a residual gas analyzer includes measuring a known sample by the sensor and obtaining data measurements at a first mass unit. A peak model function is fitted to the data to determine an existence of a peak. The peak model function is aligned to the data using dynamic time warping to determine peak features. It is determined whether a position of a peak center and a peak width are within a predetermined tolerance and, if so, the previous steps are performed for a next mass unit. If the position peak center or the peak width at the first mass unit are outside the predetermined tolerance, a sensor parameter is adjusted and another iteration of the calibration is performed. A signal is issued after a maximum number of iterations has been performed and the peak center and width are outside the predetermined tolerance.

14 Claims, 10 Drawing Sheets

(58) Field of Classification Search
USPC .................................................. 250/281, 282
See application file for complete search history.

(56) References Cited

U.S. PATENT DOCUMENTS

| | | | |
|---|---|---|---|
| 2004/0195500 A1* | 10/2004 | Sachs | G16B 40/10 |
| | | | 250/282 |
| 2005/0056079 A1 | 3/2005 | Nagy et al. | |
| 2019/0137465 A1 | 5/2019 | Mizutani et al. | |
| 2022/0236240 A1 | 7/2022 | Jünemann | |

OTHER PUBLICATIONS

International Bureau of WIPO; International Preliminary Report on Patentability; International Application No. PCT/US2023/029925; Date of Issuance: Feb. 4, 2025; 6 pages.

* cited by examiner

METHOD OF AUTO TUNING ONE OR MORE SENSORS

CROSS REFERENCE TO RELATED APPLICATION

This application is a national stage application pursuant to 35 U.S.C. § 371 of International Application No. PCT/US2023/029925, filed on Aug. 10, 2023, which claims priority to, and the benefit of, U.S. Provisional Patent Application 63,397,471, filed Aug. 12, 2022, and entitled "METHOD OF AUTO TUNING ONE OR MORE SENSORS," the entirety of which is incorporated herein by reference.

Technological Field

This disclosure is generally related to the field of sensors and an automated method of tuning or calibrating one or more sensors. The disclosure is specifically related to an automated method of tuning one or more sensors of a residual gas analyzer.

BACKGROUND

Efficient manufacturing is the result of many variables including efficient use of resources. The resources used in manufacturing include material resources as well as human resources. In many manufacturing processes, especially the manufacturing of scientific equipment, the human resources may be scarcest resource. Accordingly, many manufacturers try to find ways to maximize the use of their human resources through the use of automation.

In the case of mass spectrometry or residual gas analyzers, part of the manufacturing process includes calibration of the sensor(s) and more specifically the mass filter section of the sensor. This may comprise running the mass spectrometer with one or more known samples to measure a mass-to-charge ratio of the ions present. The sensor(s) are then adjusted so that the resulting spectral peaks correspond to the expected mass-to-charge ratio of the known sample. Such calibrations are manually carried out by technicians and can be time consuming and mundane. In as much as manual calibration requires the technician to go through a step wise process, human error can result in one or more calibration steps being missed or performed incorrectly. Since technicians are required to perform the manual calibration, fewer technicians are then available to troubleshoot other problems that require more in-depth analysis and specialized expertise to solve. This can produce manufacturing delays due to the time required to manually calibrate the sensor(s) and lingering manufacturing problems that cannot be resolved in a timely manner. Moreover, these lingering manufacturing problems could result in wasted materials and an overall increased cost.

These are just some of the problems associated with manufacturing processes and more specifically, the process of manufacturing a mass spectrometer.

SUMMARY

An embodiment of a method for automatically calibrating a sensor for a residual gas analyzer includes: (a) measuring a standard sample by the sensor; (b) obtaining data measurements from the sensor pertaining to the measured standard at a first mass unit; (c) fitting a peak model function to the measured data; (d) determining an existence of a peak in the data measurements via the peak model function; (e) aligning the peak model function to the data using dynamic time warping; (f) determining one or more peak features within the data measurements via the dynamic time warping; (g) determining whether a position of a peak center and a peak width are within a predetermined peak tolerance and peak width tolerance range; (h) repeating steps (b)-(g) for a next mass unit if the position of the peak center and the peak width for the first mass unit are within the predetermined tolerance ranges; (i) adjusting at least one sensor parameter when the position of the peak center or the peak width are outside the predetermined tolerance; (j) repeating steps (b)-(i) until the predetermined tolerances are met or a maximum number of iterations are performed; and (k) issuing a signal after the maximum number of iterations has been performed and the position of the peak center and the peak width for the first mass unit are not within the predetermined tolerance ranges. The signal indicates that technician intervention is required.

In an embodiment of the method, the calibration method is stopped after the signal is issued. In an embodiment, the method further includes calibrating the first mass unit and each next mass unit from a predetermined slate of mass units, wherein calibration of the predetermined slate of mass units results in calibration for an entire mass spectrum. In an embodiment, the maximum number of iterations is between three (3) and six (6) iterations. In an embodiment, the at least one sensor is a mass filter sensor. In an embodiment, the predetermined peak tolerance is 0.05 AMU of an actual value. In a further embodiment, adjusting the at least one sensor parameter further comprises adjusting at least one of a DC and an RF voltage setting. In another embodiment, the peak model is Gaussian.

Another embodiment of a method for automatically calibrating a sensor for a residual gas analyzer includes configuring one or more data storage devices to store a plurality of computer-readable instructions configured to be executed to: (a) select a mass unit from a predefined slate of mass units; (b) determine a base tune for the mass unit using historical parameter data from one or more previous tunings; (c) perform an iteration of peak width tuning until the peak width is with a predetermined tolerance, wherein a maximum number of iterations of peak width tuning is assigned; (d) perform an iteration of mass accuracy tuning until the mass accuracy is within a predetermined tolerance, wherein a maximum number of iterations of mass accuracy tuning is assigned; (e) move to a next mass unit from the predefined slate of mass units and repeat (b)-(d); (f) issue a warning signal. The warning signal is used when at least one of: (i) the maximum number of iterations of peak width tuning is reached before the peak width is tuned within the predetermined tolerance, or (ii) the maximum number of iterations of mass accuracy tuning is reached before the peak width is tuned within the predetermined tolerance. The warning signal results in stoppage of the sensor calibration.

In an embodiment, calibration at the first mass unit and each next mass unit from a predetermined slate of mass units results in calibration for an entire mass spectrum. In an embodiment, the maximum number of iterations of peak width tuning is between three (3) and six (6) iterations. In an embodiment, the maximum number of iterations of peak accuracy tuning is between three (3) and six (6) iterations. In an embodiment, the at least one sensor is a mass filter sensor. In another embodiment, the predetermined tolerance of the mass accuracy is 0.05 AMU of an actual value.

BRIEF DESCRIPTION OF DRAWINGS

A more particular description of the invention briefly summarized above may be had by reference to the embodiments, some of which are illustrated in the accompanying drawings. It is to be noted, however, that the appended drawings illustrate only typical embodiments of this invention and are therefore not to be considered limiting of its scope, for the invention may admit to other equally effective embodiments. Thus, for further understanding of the nature and objects of the invention, references can be made to the following detailed description.

FIGS. 5B1-4 illustrate an example of the tuning method showing a progression of data processing during a single iteration.

DETAILED DESCRIPTION

The following discussion relates to a method to auto tune a mass spectrometer. It will be understood that the herein described versions are examples that embody certain inventive concepts as detailed herein. To that end, other variations and modifications will be readily apparent to those of sufficient skill. In addition, certain terms may be used throughout this discussion in order to provide a suitable frame of reference with regard to the accompanying drawings. These terms may include "upper", "lower", "forward", "rearward", "interior", "exterior", "front", "back", "top", "bottom", "inner", "outer", "first", "second", and the like and are not intended to limit these concepts, except where so specifically indicated. The terms "about" or "approximately" as used herein may refer to a range of 80%-125% of the claimed or disclosed value. With regard to the drawings, their purpose is to depict salient features of a mass spectrometer and the disclosed auto tuning method and are not specifically provided to scale.

Figure 1:
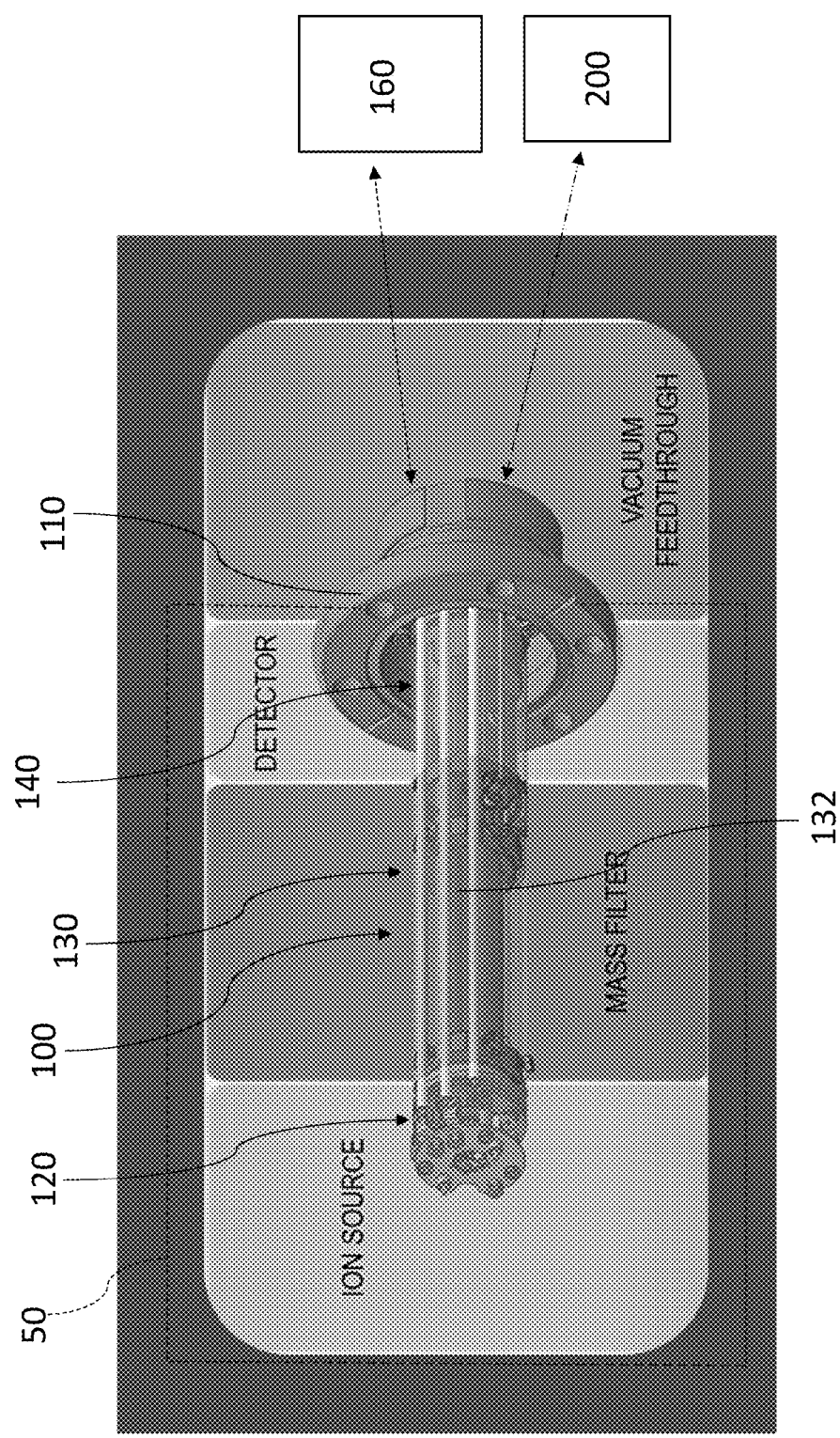
FIG. 1 illustrates a perspective view of an embodiment of a sensor used in a residual gas analyzer.

Referring to FIG. 1, an example of a sensor 100 for a mass spectrometer is shown. The sensor 100 includes a flange 110 that couples the sensor 100 to a mass spectrometer (not shown) such that the majority of the sensor 100 is positioned within a vacuum chamber 50 of a mass spectrometer shown schematically as a dotted line. A plurality of feedthroughs are disposed in the flange 110 and enable electrical connections to be made from one side of the flange 110 to the other, such as between components in the vacuum chamber 50 and components outside the vacuum chamber 50. The sensor also includes an ion source 120, a mass filter 130 and a detector 140.

Figure 2:
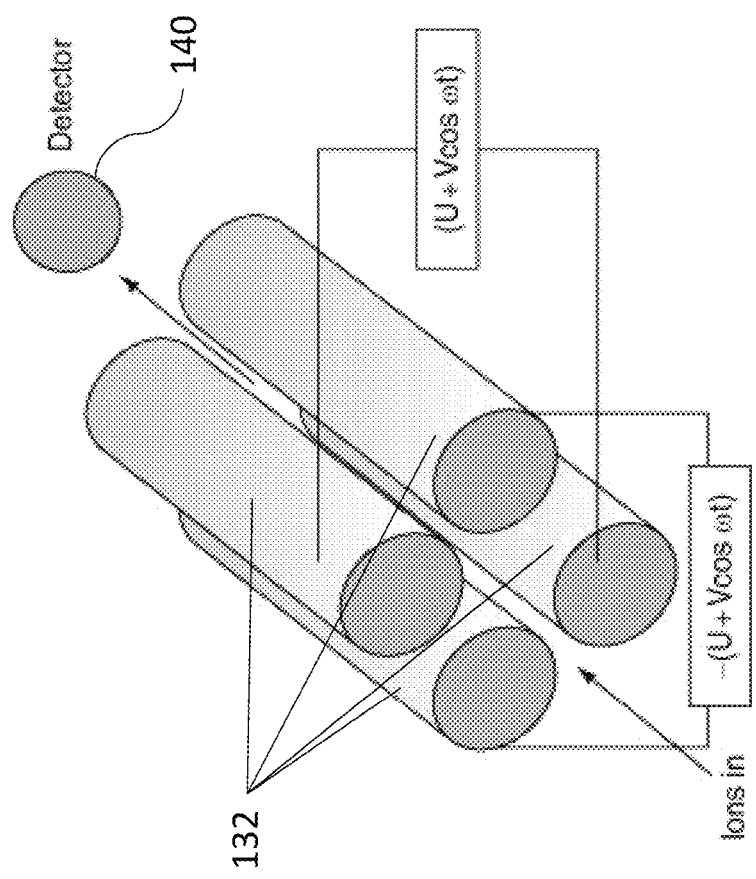
FIG. 2 illustrates a perspective view of embodiments of parallel rods used in a mass filter.

The ion source 120 that is structured to be positioned inside the vacuum chamber 50. The ion source includes an electron source, such as a filament, that generates electrons. The electrons strike molecules of the gas sample and create ions. The ions are then directed into the mass filter 130, in this case a quadrupole mass filter. Referring to FIG. 2, the mass filter 130 includes four (4) parallel rods 132 with fixed DC (U) and alternating RF ($V_0$) potentials applied between them. The potentials enable certain ions to pass between the rods 132 and into the detector 140, while other ions are deflected due to the potentials and do not enter the detector 140. The potentials between the rods 132 are controlled by a controller 160 and can be changed to vary the DC and RF potentials. Theoretically, varying the DC and RF potentials while keeping their ratio constant (i.e., linear) will scan the entire mass spectrum since each DC and RF combination along the slope will only allow one mass unit to pass between the rods 132 and to the detector 140. In practice, however, holding the ratio between potentials constant leads to an inaccurate representation of the mass spectrum. Rather, it is seen that varying the DC and RF potentials according to a piecewise linear function produces a sufficiently accurate mass spectrum.

The detector 140 detects the ions that pass through the mass filter 130 and determines the signal intensity of the ions as a function of a mass-to-charge ratio. The molecules in the sample are identified by correlating a mass of the entire sample molecule to identified masses or through a characteristic fragmentation pattern. For example, an entire mass spectrum of a sample gas may include a plurality of spectral peaks at various mass-to-charge ratios which are used to determine the composition of the sample gas. Therefore, it is important that the sensor(s) be properly calibrated so that characteristic peaks appear where they would be expected to appear if a certain molecule is present. For example, if chlorine is present in the sample, one would expect to see peaks at 35 and at 37, where the peaks have a 3:1 ratio reflecting the abundance of the two chlorine isotopes.

Up to now, calibration of the sensor(s) has been done manually, however disclosed herein is an inventive method for automating the calibration of the sensor(s), thereby increasing the time a technician has to monitor and deal with other more substantive problems that may arise during the manufacturing process. Not only does this automation increase the throughput of calibration efforts when calibrating multiple sensors at the same time (in parallel to each other), but it also increases the consistency since potential human errors are eliminated. The calibration method described herein may carried out by a separate control system 200 that is in electrical communication with the sensor(s) solely for calibration. Once connected, the control system I capable of automatically carrying out the method with little to no human intervention. In another embodiment, the controller 160 of the mass spectrometer or residual gas analyzer can be configured to perform the calibration such that subsequent calibrations can be performed by the end user or customer after the initial calibration is performed by the manufacturer. Accordingly, once the end user initiates the calibration process, it runs automatically with little or no human interference. The disclosed method is configured to be carried out by the manufacturer and/or the end user/customer.

The disclosed automated calibration method takes into account an actual sensor measurement of a standard or known sample and then changes one or more parameters of the sensor(s) to result in one or more desired spectral peak(s). This is an iterative process where the accuracy of each iteration is determined before a decision is made whether to perform another iteration, end the process or issue a notice for further investigation. For instance, if the accuracy is not within a desired tolerance, another iteration may be automatically performed. Alternatively, if the accuracy is within the desired tolerances, then the calibration process ends. After a predetermined maximum number of iterations are performed without meeting the predetermined accuracy requirements, the process outputs an "incomplete" message or other notification indicating that technician intervention may be required.

Figure 3:
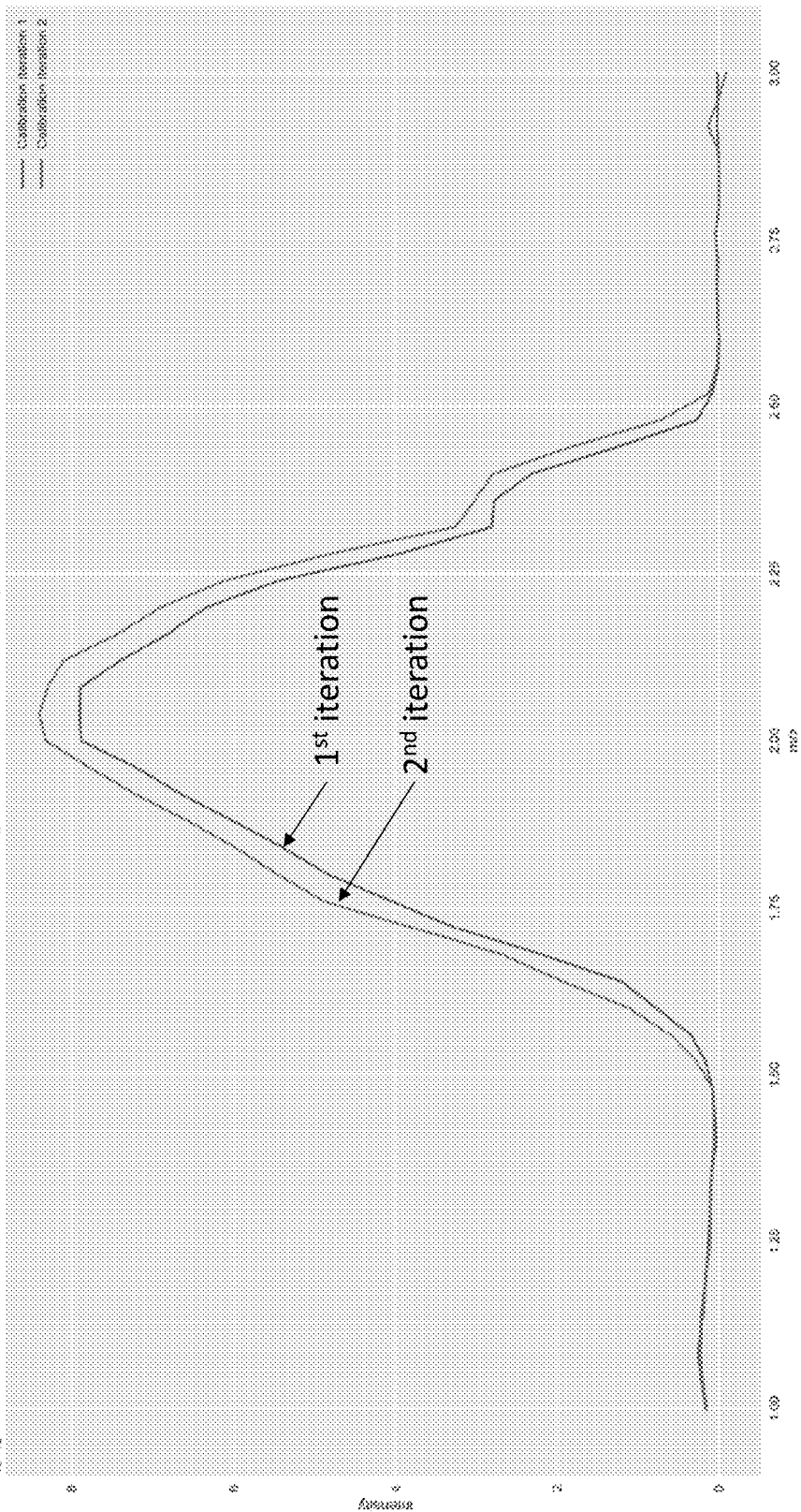
FIGS. 3 and 4 illustrate examples of a peak function fitted to data taken in a spectrum of 1-3 m/z.
Figure 4:
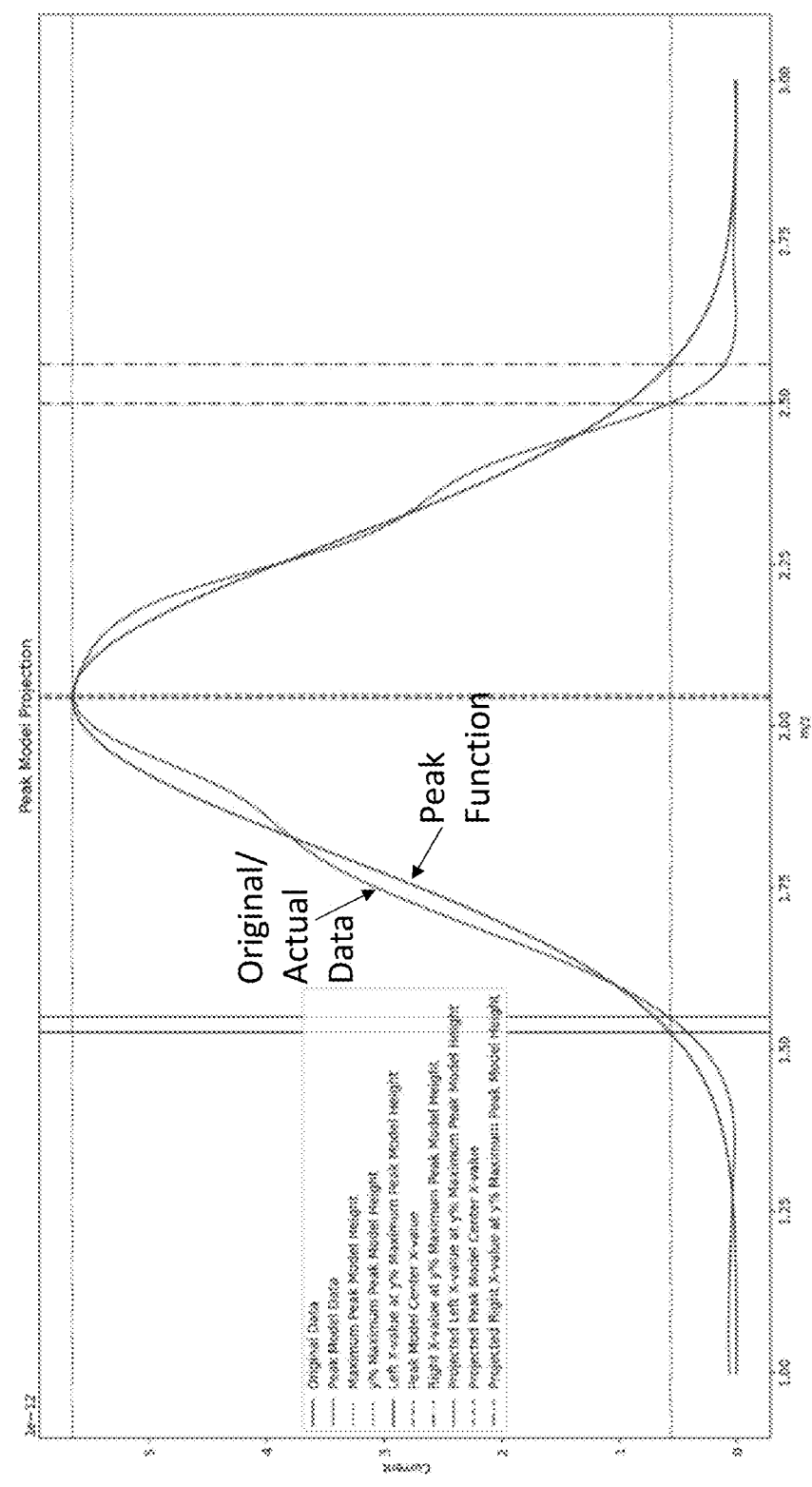

The method begins by introducing a known or standard sample into the to the sensor(s) 100. The standard sample may be any composition. Since the known sample is being analyzed by the sensor(s) 100 in a controlled environment, such as a vacuum chamber 50 of a mass spectrometer or residual gas analyzer, one would expect spectral peaks at certain m/z values. For example, if the standard sample includes helium, then one would expect a spectral peak at or around 2 m/z. This being the case, only a certain mass-to-charge range needs to be scanned for data points. Referring to FIGS. 3-4, data collected by the detector is shown from 0-3 m/z. The data detected by the detector is shown in a non-smooth curve. A function, such as a peak model function, is then fit to the data and is shown as a smooth curve. The peak function is fit to the data in an effort to smooth out the data. In an embodiment, the peak function may be Gaussian as shown in FIG. 4. A Gaussian distribution not only refers to the Normal distribution but also to variants and derivatives of the Gaussian distribution. In other embodiments the peak function may not be Gaussian. Performing curve fitting with nonlinear least squares is discussed and is one example, other modeling approaches are equally viable.

The smooth function is then aligned to the non-smooth data (original or actual data) using dynamic time warping, which is an algorithm for measuring similarity between two temporal sequences. The data, and subsequently the function, may be multidimensional. The dynamic time warping algorithm finds the optimal aligning path permitting derived peak placement and signal quality features. This alignment of the peak function and the original data enables an assessment of signal quality and signal noise of the actual data or features of the actual data. In other words, the peak function identifies whether or not a peak exists in the actual data, and data mining the results of the dynamic time warping process identifies peak features within the data. The fit or magnitude of the alignment of the peak function with the actual data can be measured and used to shift between the peak function and the data itself. In this way the data that the peak function is based on can be used for analysis. The greater the magnitude of the alignment of the peak function and the actual data, the less likely that the peak function is a realistic model for the obtained data.

The location of the peak center is measured to determine whether it is within the predetermined accepted tolerance or deviation by comparing the location of the peak center with the user defined optimal locale. For example, in the case of helium, the user defined optimal locale of the peak center would be 2 m/z. If the measured peak center locale is outside the predetermined accepted tolerance, then an optimization algorithm is used to adjust a parameter of the sensor(s) to try to find the setting that has the closest alignment to the peak function and be within the predetermined tolerances. The optimization algorithm may generally adjust the parameters using the Newtonian Method, however other root-finding and optimization (e.g., stochastic gradient descent, particle swarm optimization) algorithms may be used to produce successively better adjustments. In the case of the Gaussian model, the optimization algorithm simply will yield the mean of the distribution. If, instead, a multimodal model is used then this optimization routine may yield a different location. In the case of the mass filter sensor 130 of a mass spectrometer, the optimization algorithm will result in the automatic adjustment of at least one of the RF and DC voltages. In an embodiment, the DC and RF voltages are simultaneously adjusted additively and/or multiplicatively. When shifting the location of the peak center, the new RF and DC voltages are extrapolated according to the piecewise linear function encapsulating how the potentials vary with the mass-to-charge ratio. Alternatively, when optimizing peak width (distance between right and left endpoints the predefined % of maximum peak height), the DC voltage is adjusted by the shift value specified and the RF voltage adjusted by ⅓ of the shift value specified. The location of the peak center is approximately controlled by adjusting the RF voltage such that, within a certain range of RF voltage, adjustments will result in a shift in the peak center but will not affect the peak width. After the adjustment is completed, another iteration of the calibration process is automatically initiated. This sequence is repeated until the predetermined tolerances are met or until a predetermined maximum number of iterations are performed. If the adjustment leads to a result that is farther away from the predetermined tolerances (predetermined accuracy), then the optimization algorithm readjusts the RF voltage either in the opposite direction or to a lesser magnitude in the same direction as the previous adjustment. In an embodiment, the predetermined tolerance may be that the peak center locale must be within 0.05 AMU of the user defined optimal locale and the maximum number of iterations may be three (3).

In addition, the width of the peak (i.e., the distance measured between the left and right peak endpoints on the vertical (Y) direction of the mass spectrum curve at a user defined percentage of the peak locale's amplitude) is compared to the user defined optimal peak width to determine whether the width of the peak is within the predetermined tolerance or deviation. If the measured width is outside the predetermined accepted tolerance, then the optimization algorithm is used to adjust a parameter of the sensor(s). Again, in the case of the mass filter sensor 130 of a mass spectrometer, the optimization algorithm will adjust the DC voltage and then another iteration of the calibration process is automatically initiated. In other words, the peak width is approximately controlled by adjusting the DC voltage such that within a certain range of DC voltage, adjustments will result in a shift of the peak width without affecting the peak center. This is repeated until the predetermined tolerances are met or until a predetermined maximum number of iterations are performed. In an embodiment, the optimal width of the peak may be, with a specified width tolerance of 0.9 AMU±0.05 AMU, from 1.55-2.50 AMU at the optimal locale of 2 m/z with a peak tolerance of 0.05 AMU and the maximum number of iterations may be three (3). Accordingly, the maximum number of iterations for the entire calibration of a single tune mass per given sensor may be six (6) (three (3) iterations each for peak center and peak width). If the predetermined tolerances are not met after reaching the maximum number of iterations, then the automatic tuning procedure is stopped, and a signal is produced indicating that the sensor must be manually checked by a technician. Any predetermined tolerances may be used and will likely vary between manufacturers and the type of sensor(s) being calibrated. If the sensor is tuned at or before the maximum number of iterations is reached, then the iteration count is set to zero (0) and tuning is automatically begun at the next mass unit in the queue.

Figure 5A:
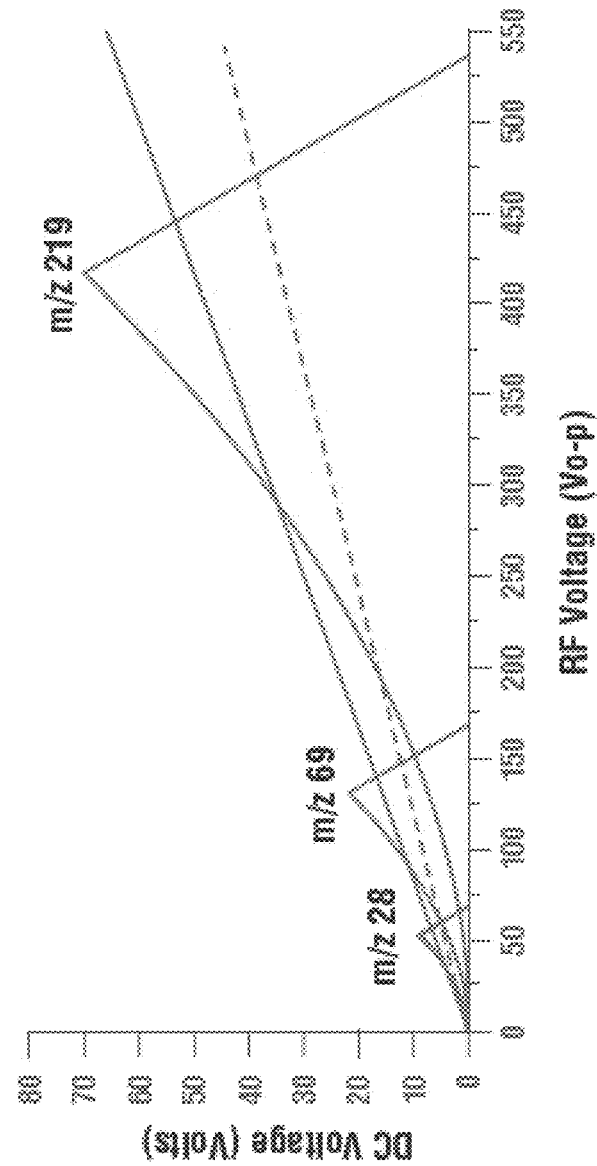
FIG. 5A is a graphical representation of an example of parameters that can be changed to tune the one or more sensors.

Referring to FIG. 5A it can be seen how changing the DC and RF voltage can affect the peak being displayed at a certain m/z. In this figure it is indicated that peaks are expected at 28 m/z, 69 m/z and 219 m/z. These values may be measured by a single sensor if the DC and RF voltages are adjusted properly. In other embodiments, the automated calibration method is performed sequentially over each tune mass over a plurality of sensors in parallel. The goal of the automated calibration method is to find the optimum DC and RF voltage where a peak is shown at the expected m/z or around the expected m/z within the predetermined tolerance ranges. The dotted line represents DC and RF values chosen in a first iteration. DC and corresponding RF voltages along this line are not close to the indicated peaks at 28, 69, and 219. The solid line represents a second iteration of the calibration process where the DC and/or the RF voltage(s) are changed such that the line has moved closer to each of the peaks. This adjustment would result in the data peaks moving closer to the accepted peak centers and accepted peak widths. The solid line shows an example of DC and RF voltage values needed to see one, two, or all three peaks.

It can be appreciated that the goal of the calibration method is to automatically calibrate the sensor(s) in as few iterations or steps as possible. The longer the calibration takes (i.e., the more iterations are run), the more time consuming and less advantageous the process becomes. In an embodiment, the optimal maximum number of iterations is from three (3) to six (6). After calibration at the final mass unit in the predetermined slate of mass units is completed, then the automatic calibration process is ended.

Figure 5B:
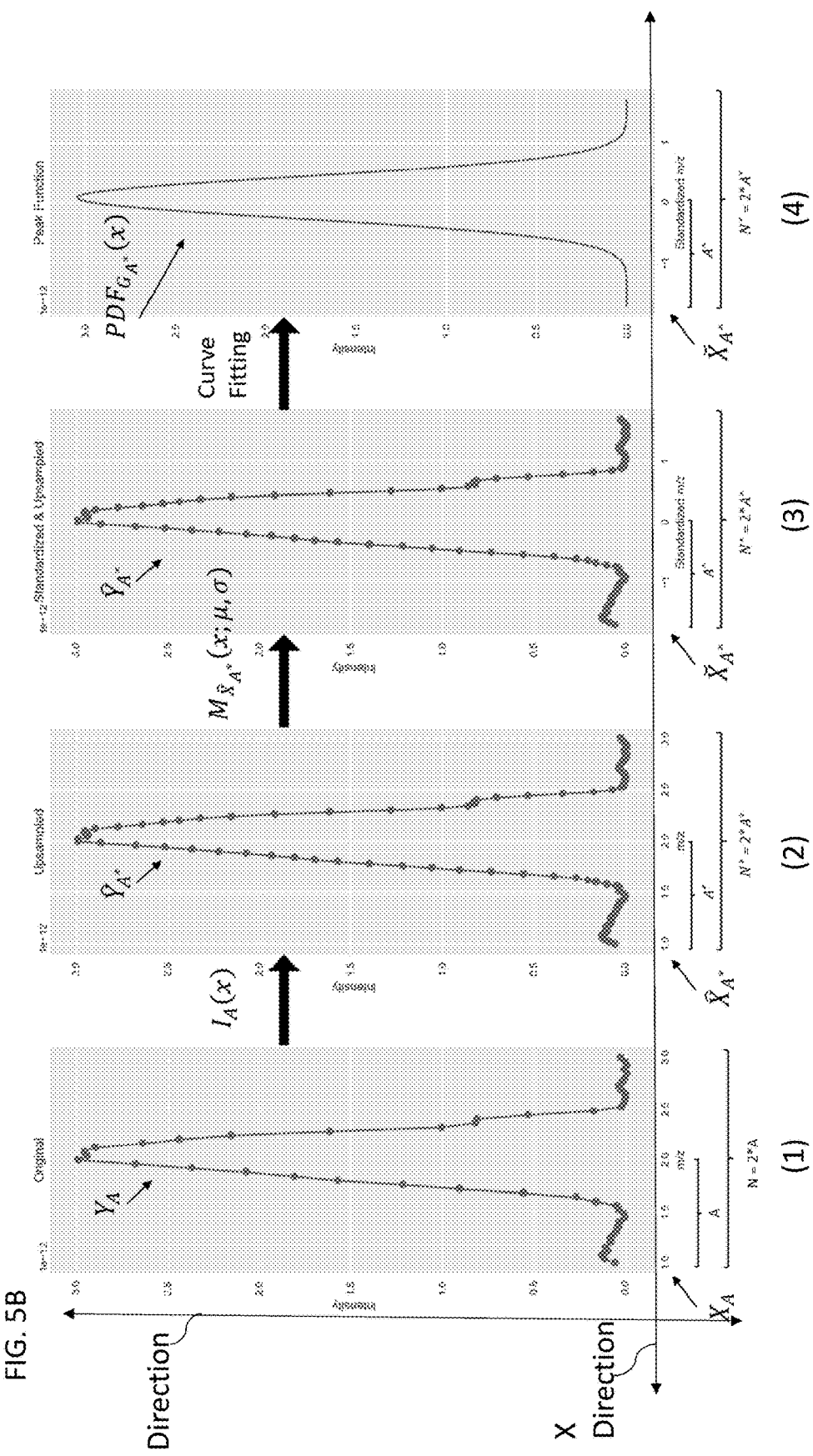
Figure 5C:
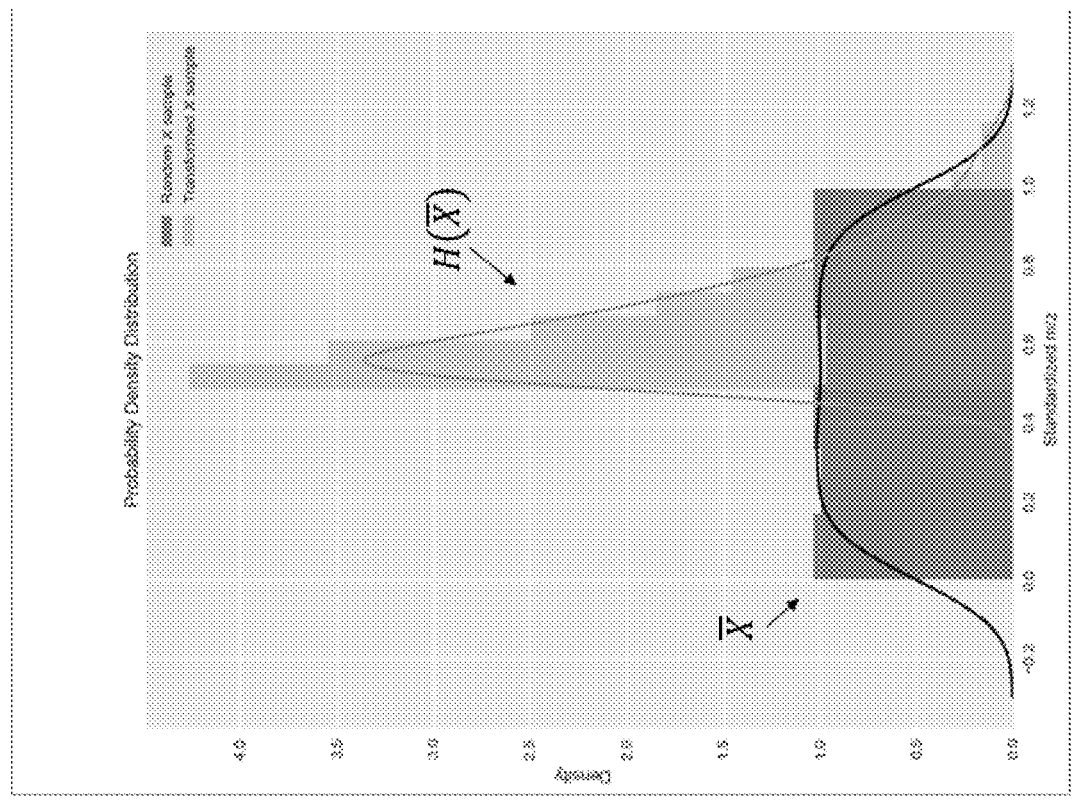
FIG. 5C illustrates another embodiment of the tuning method showing the transformation of an original data distribution.

FIGS. 5B1-4 (and also referring to Appendix I) represent an embodiment of the signal processing method described where original measurement data is obtained from a known sample in FIG. 5B1. The data is then fit with a function, such as a cubic spline. In FIG. 5B2 the data is then interpolated such that it is up-sampled to increase the resolution (i.e., provide more data points) by model fitting. In FIG. 5B3, the data is normalized in the horizontal (X) direction such that the center of the data peak is positioned at zero (0) with a normal distribution of data to either side. This normalization is accomplished by subtracting each data point X value from the mean (in this case mean=2) and divide by the standard deviation. This will result in data that is normally distributed along the X direction. In FIG. 5B4, a model function is fitted to the normalized data. As shown, the data is fitted with a Gaussian function, however other embodiments may be fitted with different functions. The peak function in FIG. 5B4 is then aligned or mapped with the interpolation function used to generate data in FIG. 5B2 (a proxy for the data in FIG. 5B1) at specific subsections using dynamic time warping. For example, mapping can be done at the region of 10% peak height on both sides of the peak and also at the peak center for each group of data (data relating to each predefined mass value being tuned). FIGS. 5B1-4 illustrate an example where the disclosed method is used to scale an original set of data $\bar{X}$ (i.e., data simulated from a specified probability distribution) to a relevant range indicated by H($\bar{X}$). The relevant range H($\bar{X}$) is then used to generate vertical (Y) data from both the peak function in FIG. 5B4 and the interpolation function used in FIG. 5B2 for the purpose of utilizing dynamic time warping to map the vertical (Y) data from the peak function onto the vertical (Y) data from the interpolation function. As can be seen in FIG. 5C, each iteration of the method acts to transform or draw the data into the theoretical center such that a peak is defined after the final iteration.

Figure 6:
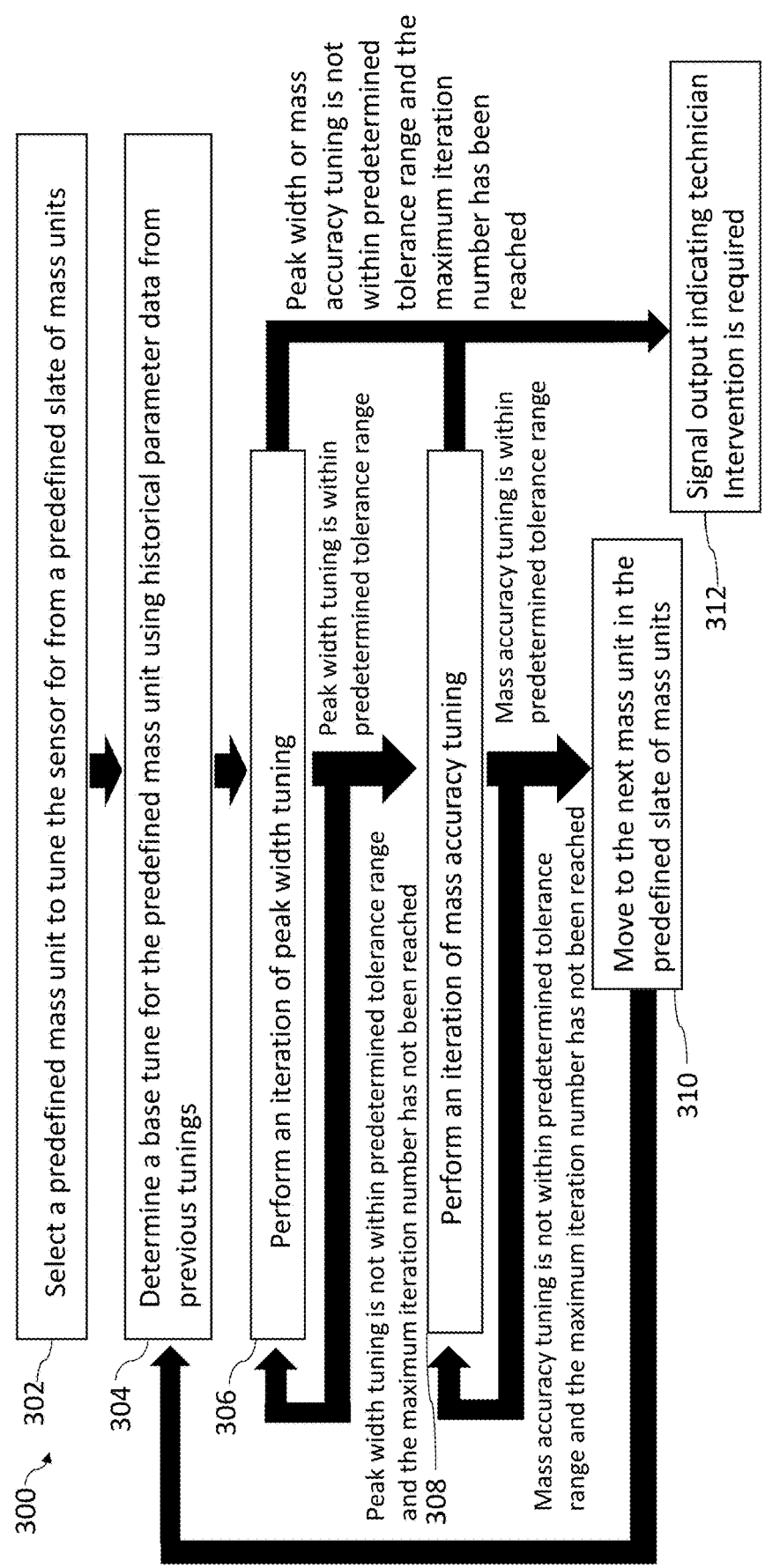
FIG. 6 schematically illustrates an embodiment of a method for auto tuning a sensor.

Referring to FIG. 6, an embodiment of the method 300 is schematically depicted. As shown, the method 300 starts at step 302 by selecting a predefined mass unit in the tune mass queue to be tuned. Each sensor is tuned at a predetermined slate of masses in the tune mass queue. In this way, the sensor is tuned across the entire mass spectrum without actually being tuned at each separate mass within the spectrum. Step 304 is then performed for each mass unit in the tune mass queue. At step 304 the system accesses parameters set at the previous tune mass and combines this information with historical parameter data from past tuned sensors to fit a conditional probability distribution function and determine the statistically most important combination of RF and DC voltage settings. This value is then set as the base tune for that specific mass.

A peak width tune 306 and a mass accuracy tune 308 is then performed using the previously described method one or more times. If the peak width and the mass accuracy are within the tolerance range after or before a predetermined tune iteration threshold is reached, then the system moves on to the next mass unit in the queue 310. If the sensor cannot be tuned at one of the specified mass units, then the automated tuning procedure stops and an "incomplete" message or warning signal is issued 312 indicating that a technician is required to intervene. At this point, the automatic calibration stops until the technician intervention has been completed and the calibration is restarted. In an embodiment, the predetermined slate of mass units and the maximum number of iterations are preloaded into the controller 160 or the control system 200 by the manufacturer. In another embodiment, the predetermined slate of mass units and the maximum number of iterations are selected by the end user.

Figure 7:
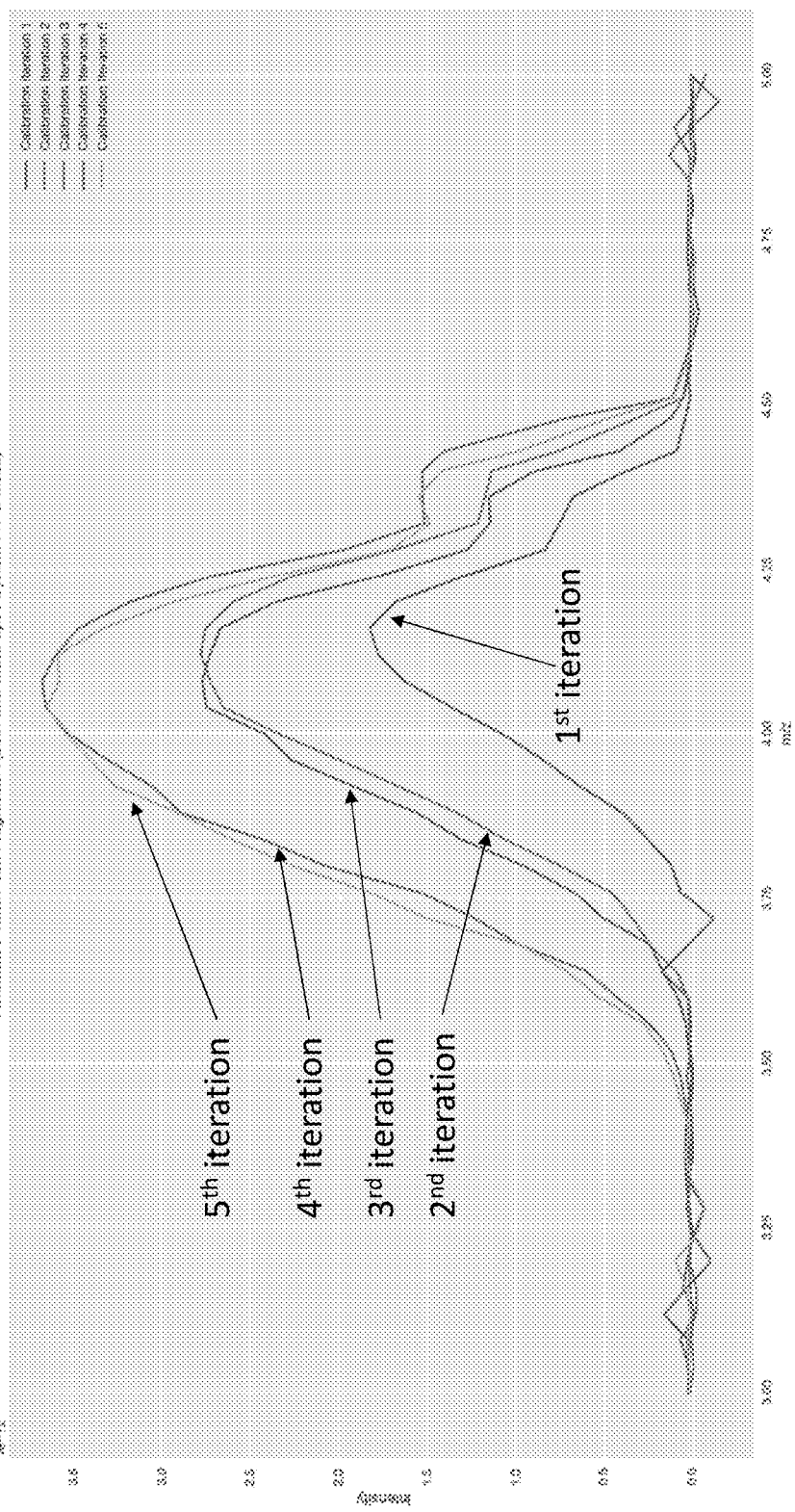
FIGS. 7 and 8 illustrate two different examples of the tuning method showing the progression of the peaks after each iteration.

Turning to FIG. 7, an example is shown having five (5) calibration iterations. In this example a peak is expected at 4 m/z so the spectral scan is performed between 3 and 5 m/z. The first iteration (lowest peak) indicated as the peak with the smallest intensity has a peak center at about 4.18 m/z. As this value is outside the predetermined tolerance for peak center, additional iterations of the correction are performed until the peak center and peak width are within the predetermined tolerance. In this example, five iterations were required with the fifth iteration producing a peak center that is at 4 m/z or within the predetermined tolerance. Likewise, the peak width at the first iteration is about 0.63 m/z, which is outside the determined tolerance. By the fifth iteration, the peak width is 0.85 m/z, which is within the predetermined tolerance. Accordingly in this example, both the peak center and width are tuned within the predetermined tolerances before the maximum number of iterations is reached.

Figure 8:
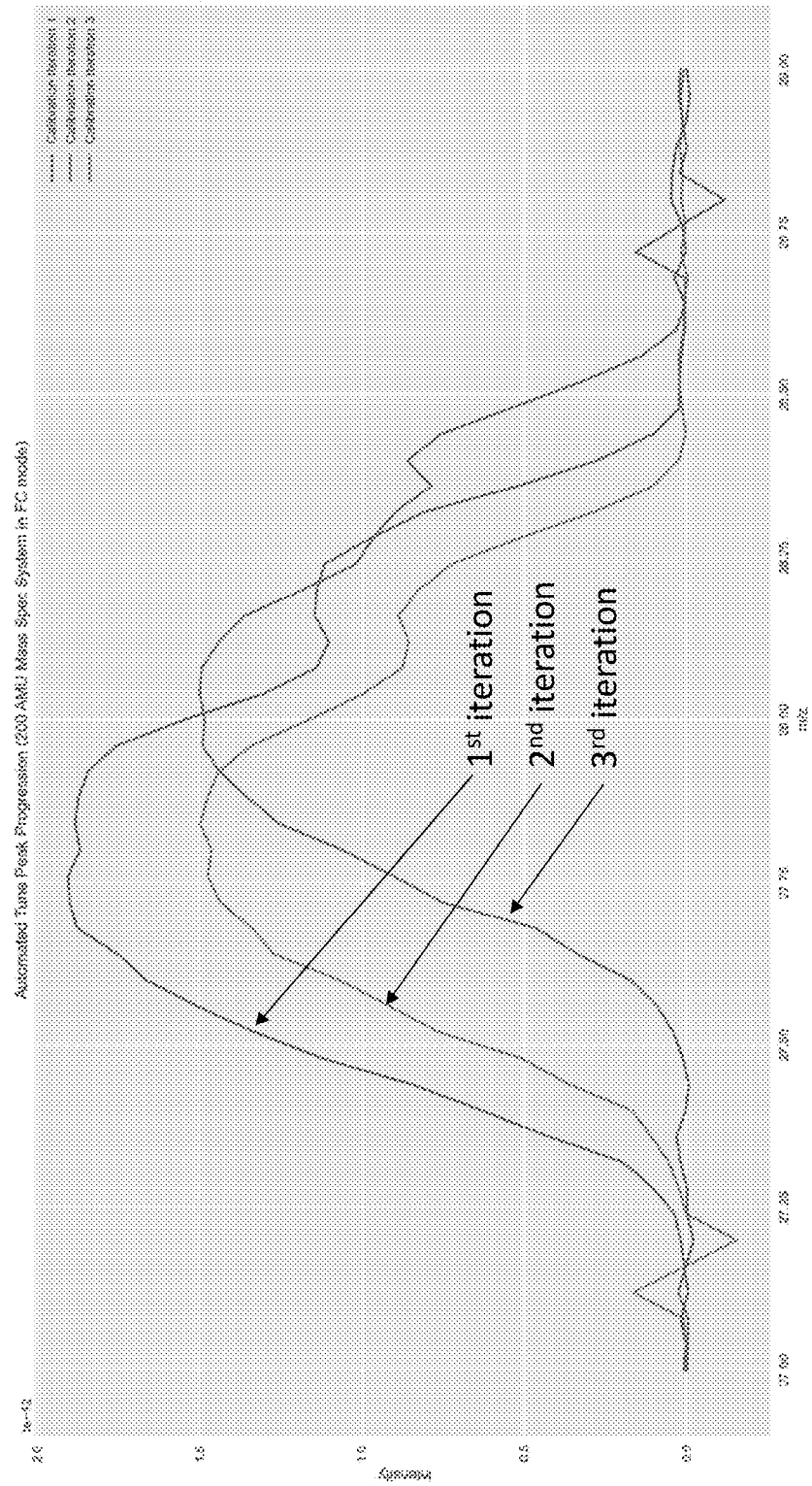

FIG. 8 illustrates another example of the calibration method. In this example, a peak is expected at 28 m/z. As can be seen, the first iteration (highest peak) is shown having a peak around 27.75 m/z. Two more iterations are run with the third iteration having a peak at 28 m/z or within the predetermined tolerance. Similarly, the peak width after the first iteration is about 1.58 m/z, which is outside of the predetermined tolerance. After the third iteration, the peak width is about 0.86 m/z, which is within the predetermined tolerance. Accordingly in this example, both the peak center and the peak width are tuned within the predetermined tolerances after the third iteration.

While this method has been describing as it related to the calibration of sensor(s) or a mass spectrometer or a residual gas analyzer, it should be apparent that the method can be tailored to enable automatic calibration of a variety of sensors for various types of equipment.

While the present invention has been particularly shown and described with reference to certain exemplary embodiments, it will be understood by one skilled in the art that various changes in detail may be affected therein without departing from the spirit and scope of the invention that can be supported by the written description and drawings. Further, where exemplary embodiments are described with reference to a certain number of elements, it will be understood that the exemplary embodiments can be practiced utilizing either less than or more than the certain number of elements.

The invention claimed is:

1. A method for automatically calibrating a sensor for a residual gas analyzer, the method comprising:
   (a) measuring a standard sample by the sensor;
   (b) obtaining data measurements from the sensor pertaining to the measured standard at a first mass unit;
   (c) fitting a peak model function to the measured data;
   (d) determining an existence of a peak in the data measurements via the peak model function;
   (e) aligning the peak model function to the data using dynamic time warping;
   (f) determining one or more peak features within the data measurements via the dynamic time warping;
   (g) determining whether a position of a peak center and a peak width are within a predetermined peak tolerance and peak width tolerance range;
   (h) repeating steps (b)-(g) for a next mass unit if the position of a peak center and a peak width for the first mass unit are within the predetermined tolerance ranges;
   (i) adjusting at least one sensor parameter when the position of the peak center or the peak width are outside the predetermined tolerance;
   (j) repeating steps (b)-(i) until the predetermined tolerances are met or a maximum number of iterations are performed; and
   (k) issuing a signal after the maximum number of iterations has been performed and the position of the peak center and the peak width for the first mass unit are not within the predetermined tolerance ranges, wherein the signal indicates that technician intervention is required.

2. The method of claim 1, further comprising stopping the calibration process after the signal is issued.

3. The method of claim 1, further comprising calibrating the first mass unit and each next mass unit from a predetermined slate of mass units, wherein calibration at the predetermined slate of mass units results in calibration for an entire mass spectrum.

4. The method of claim 1, wherein the maximum number of iterations is between three (3) and six (6) iterations.

5. The method of claim 1, wherein the at least one sensor is a mass filter sensor.

6. The method of claim 1, wherein the predetermined peak tolerance is 0.05 AMU of an actual value.

7. The method of claim 5, wherein the adjusting the at least one sensor parameter further comprises adjusting at least one of a DC and an RF voltage setting.

8. The method of claim 1, wherein the peak model is Gaussian.

9. A method for automatically calibrating a sensor for a residual gas analyzer, comprising:
   configuring one or more data storage devices to store a plurality of computer-readable instructions configured to be executed to:
   (a) select a mass unit from a predefined slate of mass units,
   (b) determine a base tune for the mass unit using historical parameter data from one or more previous tunings,
   (c) perform an iteration of peak width tuning until the peak width is with a predetermined tolerance, wherein a maximum number of iterations of peak width tuning is assigned,
   (d) perform an iteration of mass accuracy tuning until the mass accuracy is within a predetermined tolerance, wherein a maximum number of iterations of mass accuracy tuning is assigned,
   (e) move to a next mass unit from the predefined slate of mass units and repeat (b)-(d),
   (f) issue a warning signal when at least one of:
      (i) the maximum number of iterations of peak width tuning is reached before the peak width is tuned within the predetermined tolerance, or
      (ii) the maximum number of iterations of mass accuracy tuning is reached before the peak width is tuned within the predetermined tolerance,
   wherein the warning signal results in stoppage of the sensor calibration.

10. The method of claim 9, wherein calibration at the first mass unit and each next mass unit from a predetermined slate of mass units results in calibration for an entire mass spectrum.

11. The method of claim 9, wherein the maximum number of iterations of peak width tuning is between three (3) and six (6) iterations.

12. The method of claim 9, wherein the maximum number of iterations of peak accuracy tuning is between three (3) and six (6) iterations.

13. The method of claim 9, wherein the at least one sensor is a mass filter sensor.

14. The method of claim 1, wherein the predetermined tolerance of the mass accuracy is 0.05 AMU of an actual value.

* * * * *